(12) United States Patent
Moles

(10) Patent No.: US 8,082,810 B2
(45) Date of Patent: Dec. 27, 2011

(54) MICROFLUIDIC ELASTIC MICRO-ALIQUOTTER

(75) Inventor: Donald R. Moles, Cedarville, OH (US)

(73) Assignee: YSI Incorporated, Yellow Springs, OH (US)

( * ) Notice: Subject to any disclaimer, the term of this patent is extended or adjusted under 35 U.S.C. 154(b) by 340 days.

(21) Appl. No.: 12/240,169

(22) Filed: Sep. 29, 2008

(65) Prior Publication Data

US 2010/0077875 A1    Apr. 1, 2010

(51) Int. Cl.
*G01N 1/14* (2006.01)
(52) U.S. Cl. ................................... 73/864.34
(58) Field of Classification Search ........................ None
See application file for complete search history.

(56) References Cited

U.S. PATENT DOCUMENTS

| | | | |
|---|---|---|---|
| 3,148,861 A * | 9/1964 | McFarland, Jr. | 251/331 |
| 4,008,621 A * | 2/1977 | Ostojic et al. | 73/864.52 |
| 5,178,021 A * | 1/1993 | Kosuth | 73/864.62 |
| 5,254,313 A * | 10/1993 | Kuroda et al. | 422/100 |
| 5,535,635 A * | 7/1996 | Shaw | 73/863.84 |
| 5,932,799 A | 8/1999 | Moles | |
| 6,431,212 B1 | 8/2002 | Hayenga et al. | |
| 6,481,453 B1 | 11/2002 | O'Connor et al. | |
| 6,585,939 B1 | 7/2003 | Dapprich | |
| 6,719,868 B1 | 4/2004 | Schueller et al. | |
| 6,929,030 B2 | 8/2005 | Unger et al. | |
| 6,951,632 B2 | 10/2005 | Unger et al. | |
| 6,960,437 B2 | 11/2005 | Enzelberger et al. | |
| 7,040,338 B2 | 5/2006 | Unger et al. | |
| 7,077,152 B2 | 7/2006 | Karp | |
| 7,097,809 B2 | 8/2006 | Van Dam et al. | |
| 7,118,910 B2 | 10/2006 | Unger et al. | |
| 7,125,711 B2 | 10/2006 | Pugia et al. | |
| 7,275,858 B2 | 10/2007 | Andersson et al. | |
| 7,306,672 B2 | 12/2007 | Hansen et al. | |
| 2002/0029814 A1 | 3/2002 | Unger et al. | |
| 2004/0005247 A1 | 1/2004 | Karp | |
| 2010/0254837 A1 * | 10/2010 | Boersma et al. | 417/413.2 |

* cited by examiner

*Primary Examiner* — Robert Raevis
(74) *Attorney, Agent, or Firm* — Thompson Hine LLP

(57) ABSTRACT

Disclosed is a microfluidic device comprising at least one micro-aliquotter for dispensing fixed or variable volumes. The micro-aliquotter includes an rigid, dimensionally stable foundational layer having a fluid port therein that is in fluid communication with a channel within the microfluidic device, and an elastic film positioned on the foundational layer where the film covers the fluid port. The elastic film is sealed to the foundational layer so fluids entering through the fluid port can be captured between the elastic film and the foundational layer. The elastic film being expandable from a rest position on the foundational layer to a dispensing, or aliquotting, position in which an aliquot volume of a fluid is contained between the film and the foundational layer.

26 Claims, 7 Drawing Sheets

MICROFLUIDIC ELASTIC MICRO-ALIQUOTTER

BACKGROUND

The present application relates generally to a device for precisely metering fluids, more particularly the application discloses a microfluidic device including a micro-aliquotter.

Microfluidic devices are useful in various applications and can be used to analyze small amounts of samples in fluid systems for contaminants, chemicals, or other analytes in the body, water systems, industrial fluid systems, or any of a variety of systems having fluid components. In many of these microfluidic based analytical systems, precise volumes of reagents and/or analytes are required. It may also be the case that these volumes be kept very small, especially in situations where the reagents may be expensive, the sample is limited or the physical space inside the analyzer is limited.

Basically, in microscale analytical systems, the precise metering of small fluid volumes is important to obtaining reliable results, and arguably, may be the most important internal function of such a system. Accordingly, there is a need for integrated fluid aliquotting devices with improved precision in metering and dispensing fixed and variable volumes of fluid in a microfluidic device. Applicant has developed a micro-aliquotter that can dispense a fixed or variable volume of fluid with improved precision. The variable volume is possible because an elastic film is used that expands in response to the fluid pressure of a fluid building up and being contained under the film and between the film and a rigid, dimensionally stable surface. Depending upon the fluid pressure applied and the time the fluid pressure is applied for a fluid, the elastic film will expand to a particular volume that can be determined in reference to a calibration curve of the micro-aliquotter for that fluid. The calibration may depend upon the fluid being aliquoted, the pressure used to move the fluid, the amount of time the pressure is applied and the mechanical characteristics of the elastic member.

Because the fluid volume inside the aliquotter is formed with the help of an elastic member, it represents a fluidic structure the volume of which can be operationally defined from essentially zero up to the designed limit. This inherent feature allows the fluidic system, in general, to be more conservative of fluids, since no additional fluid movement is required to displace the resulting aliquoted volume.

SUMMARY

Disclosed herein is a microfluidic device having a micro-aliquotter for metering the volume of a fluid. The micro-aliquotter is capable of metering small fixed or variable volumes of fluid, such as volumes of about 5 µL to about 100 µL. The microfluidic device comprises at least one micro-aliquotter having a dimensionally stable foundational layer having a fluid port therein that is in fluid communication with a channel within the microfluidic device and having an elastic film positioned on the foundational layer that covers the fluid port. The elastic film is sealed within the microfluidic device so fluids discharged from the fluid port are captured between the film and the foundational layer and cannot flow through or around the film. The elastic film is expandable from a rest position in which it lies flat on the foundational layer to a dispensing position in which an aliquot volume of a fluid is contained between the film and the foundational layer. In the rest position, in one embodiment, the elastic film lies on the foundational layer such that there is substantially little to substantially no space (aliquot volume) between the film and the foundational layer. In the rest position the elastic film can be stretched or unstretched.

In one embodiment, the micro-aliquotters disclosed herein may be reusable with different fluids if the micro-aliquotter is flushed to remove any remnant fluid and the start up and calibration procedures discussed below are used with the new fluid to be aliquoted. The micro-aliquotter may also be disposable.

In another embodiment, the micro-aliquotter may include a chamber that includes a space for receiving a hydraulic or pneumatic pressure to actively discharge the aliquot. The chamber may include a first fluid port in a first wall, a second fluid port in a second wall, and an elastic film positioned on the first wall where the film covers the first fluid port and defines a space between the elastic film and the second wall. The elastic film is sealed within the microfluidic device so a first fluid entering through the first fluid port is captured between the film and the first wall and cannot flow to the second fluid port and a second fluid from the second fluid port cannot flow to the first fluid port. The elastic film captures an aliquot volume between the elastic film and the first wall in response to the first fluid moving into the chamber through the first fluid port. The captured aliquot volume may thereafter be discharged as a result of pressure via the second fluid. The first fluid port is in fluid communication with a first channel within the foundational layer and the second fluid port is in fluid communication with a second channel in an external layer or another layer of the micro-aliquotter.

The micro-aliquotter may be used to meter a fluid volume according to a method that includes providing a micro-aliquotter of one of the embodiments disclosed herein. The micro-aliquotter has a fluid port that is in fluid communication with a channel within the microfluidic device that has a fluid in the channel. The method includes loading an aliquot volume of the first fluid between the elastic film and the foundational layer and dispensing the aliquot volume.

DETAILED DESCRIPTION

Figure 1:
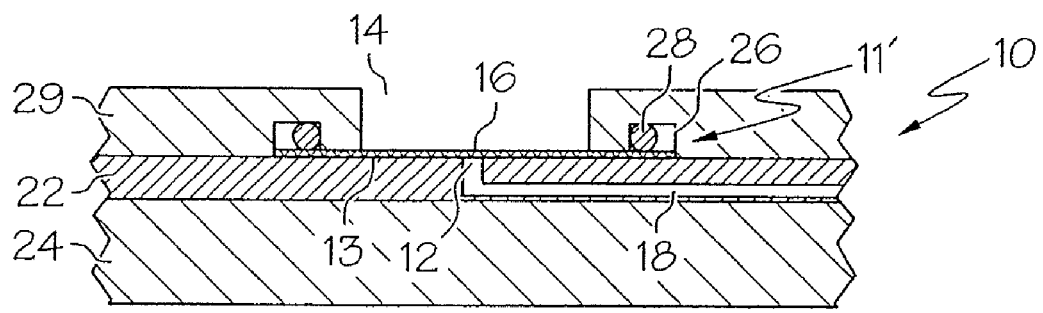
FIGS. 1 and 2 are partial sectional views of a microfluidic device showing one embodiment of a micro-aliquotter.
Figure 2:
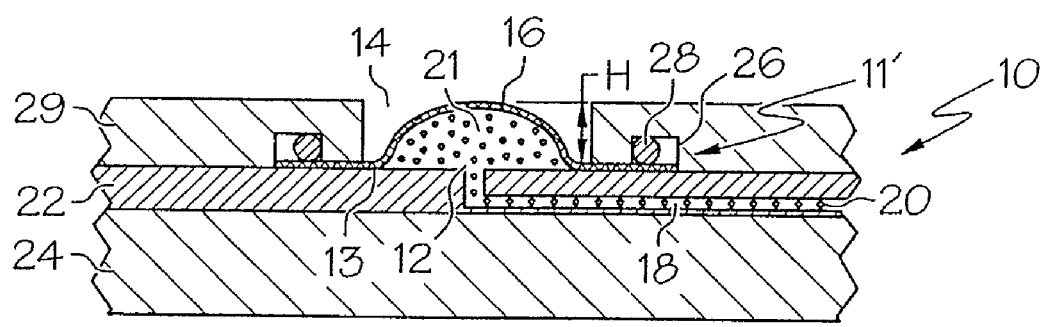

Referring to FIGS. 1 and 2, a portion of a microfluidic device in accordance with one embodiment, generally designated 10, is shown that includes a micro-aliquotter for metering an aliquot volume 21 of a fluid substance 20. The micro-aliquotter, in the embodiment shown in FIGS. 1 and 2, is formed in a partially exterior layer 29 of the microfluidic device 10 and is exposed to the outside environment through a space 14. The micro-aliquotter 11 includes a foundational layer 22 having a fluid port 12 that is in fluid communication with a channel 18 of the microfluidic device 10. The fluid port 12 may be in the upper surface 13 or the lower surface 17 of the foundational layer 22. The foundational layer 22 provides a substantially planar rigid, dimensionally stable surface to support an elastic film 16. The foundational layer 22, in cooperation with the elastic film 16, produces reproducible aliquot volumes when controlled pressure is applied to fluid substance 20.

The elastic film 16 is positioned on the foundational layer 22 with the film covering the fluid port 12. The elastic film 16 is securely sealed against the foundational layer 22, particularly whichever surface thereof that has the fluid port 12, so fluids entering through the fluid port 12 must be captured between the elastic film 16 and the foundational layer 22 and cannot flow through or around the elastic film 16. The elastic film 16 is expandable from a rest position 11 on the foundational layer 22, shown in FIG. 1, to a dispensing position 11' having an aliquot volume 21 of the fluid 20 captured between the elastic film 16 and the foundational layer 22, as shown in FIG. 2.

A micro-aliquotter formed in the exterior layer and exposed to the environment would provide the advantage of knowing if the elastic film ruptured due to over pressurizing the fluid captured thereunder. If the elastic film ruptured, the fluid would leak through and would be readily observed. Additionally, the elastic film would not have a chamber sealing above it that may contain imperfections or ports with edges that may rupture the film upon contact.

The elastic film 16 may have its perimeter fixed to the foundational layer 22 (i.e., adhered, bonded, laminated, or the like) and/or extend between the layers of the microfluidic device 10 or alternately may be fixed to a wall of a chamber. In the embodiment shown in FIGS. 1 and 2, the elastic film is fixed between layers 22 and 29 of the microfluidic device. An annular channel 28 may be formed in the lower surface of layer 29 and may receive a compressible-elastomeric material, like an O-ring, therein. The lower surface of layer 29 may then be placed against the elastic film on the foundational layer 22 to compress the compressible-elastomeric material there against to form a seal. The micro-aliquotter may be substantially circular in shape, which makes an O-ring a good choice, but the micro-aliquotter is not limited to a circular shape.

The elastic film 16 is fixed within the microfluidic device such that the film is at least partially expandable, particularly the portion of the film covering the fluid port 12, to respond to external pressure applied to fluid 20 through the fluid port 12 to be contained under the elastic film 16. When the elastic film expands in response to the fluid 20 pressure an aliquot volume 21 is captured between the elastic film 16 and the foundational layer 22 as shown in FIG. 2 in the dispensing position 11'. The elastic film 16 when moved to a maximum aliquot position will have a height H. The term "fluid," as used herein, includes any material that is capable of flowing through the channels, ports, chambers, or the like, especially gases, liquids, and solutions, suspensions, or dispersions of materials in gases or liquids.

Fluid 20 is pumped or pushed into and through the channel 18 by increasing the fluid pressure of the fluid. The channel 18 may be connected to a reservoir holding the fluid to be discharged and metered by the micro-aliquotter. The reservoir containing the fluid has a headspace that is pressurized to push the fluid from the reservoir. The reservoir may be internal or external to the microfluidic device and may have a positive displacement pump with a by-pass loop that includes a pressure drop to control the pressure applied to pump the fluid. The pressure pushing the fluid 20 through the channel should not be so large that it ruptures the elastic film 16 and the fluid 20 should be pumped slowly without a pressure drop to keep any dissolved gases within the fluid. Alternately, it may be possible to capture a plurality of fluids of known volume in the micro-aliquotter. A predetermined volume a first fluid that is less than the maximum aliquot volume may be pumped or pushed through the fluid port 12 to be captured between the elastic film 16 and the foundational layer 22. The volume of the first fluid may be metered, such that the predetermined volume of the first fluid is known. Then a second fluid may be pumped or pushed through the fluid port 12 to be captured with the first fluid between the elastic film 16 and the foundational layer 22. The second fluid is added until the maximum aliquot volume is reached. The volume of the second fluid will be equal to the difference of the maximum aliquot volume and the predetermined volume of the first fluid. The first and second fluids may then be discharged together as a mixture.

The rest position 11 has the elastic film 16 lying on the foundational layer 22 such that there is substantially little to substantially no space (aliquot volume) between the film and the foundational layer. The position of the elastic film 16 on the foundational layer makes it possible to discharge substantially all of the aliquot volume, which is advantageous because the volume measurement should be more accurate.

The elastic film 16 may be made of or include an elastomeric material such as polyurethane, polyimide, polyethylene, polyvinylchloride, or other material known to one of skill in the art, typically possessing a Young's modulus of less than 2000 MPa (megapascals). One of skill in the art will appreciate that the elastomeric material selected may depend upon the particular application the microfluidic device will be used for, including whether the elastic film will be in an exposed embodiment like FIGS. 1 and 2 or an enclosed embodiment like FIGS. 5-8. The embodiment shown in FIGS. 1 and 2 should have an elastic film 16 that has nearly perfect elasticity so that the elasticity of the film itself can supply the pressure needed to discharge the aliquot volume 21. The fluid pressure used to move the fluid 20 under the elastic film 16 will need to be stopped and any appropriate valves opened or closed to allow the elastic film 16 to return to the rest position due to its elasticity and thereby discharge the aliquot volume. The elastic film 16 whether exposed or enclosed should be one that is chemically resistant to the fluids being aliquoted (i.e., will not chemically react or degrade in the presence of the fluid over time, etc.) and to the environmental/ambient conditions the film will be exposed. A gas from the environment may permeate the film 16 and dissolve in the fluids within the microfluidic device 10, which may negatively affect the stability of the sample, or the reagents. Where this is a concern a gas impermeable film should be used, for example, Saranex, a composite film composed of polyvinylidene chloride and polyethylene, available from Dow Chemical. The elastic film may be about 25 to 50 microns thick in accordance with one embodiment.

While the elastic film is an elastomeric material, the foundational layer 22 or at least a substrate layer 24 upon which the foundational layer 22 is positioned is formed from a substantially rigid dimensionally stable material. If the foundational layer 22 is relatively thin, and as such, has some degree of flexibility that could affect the precision of the micro-aliquotter a substrate layer 24 may be included to support the foundational layer 22. The presence of the channel 18 and potentially additional channels, reservoirs, valves, manifolds, and other features for controlling the flow of fluids in microfluidic devices known of one of skill in the art may contribute to the flexibility of a thin foundational layer. The substrate layer 24 should keep the foundational layer 22 relatively planar throughout the operation of the micro-aliquotter to increase precision and/or accuracy in containing and dispensing the aliquot volume 21. The substrate layer may be a variety of materials such as metal, plastics, glass, polymers or other materials known to one of skill in the art that would provide the necessary stiffness to preclude the flexing of the foundational layer 22 on a scale that would affect the aliquot volume.

Still referring to FIGS. 1 and 2, the exterior layer 29 or at least the portion against the elastic film 16 is a substantially rigid, dimensionally stable material. The exterior layer 29 and the foundational layer 22 may be the same material or different. In one embodiment, the foundational layer 22 is a thermoplastic material that may be injection molded to a thickness sufficient to provide rigidity. The thermoplastic material should be able to have a channel formed therein and the surface features, described below, formed thereon. A variety of rigid, dimensionally stable materials are known to one of skill in the art, or polymeric materials such as plastics, for example polymethylmethacrylate (PMMA), polycarbonate, polytetrafluoroethylene (TEFLON™), polyvinylchloride (PVC), polysulfone, polyamide, and polyimide, and the like. Alternately silica based substrates may be used for the foundational layer, such as glass, quartz, silicon, polysilicon, and the like.

Figure 3A:
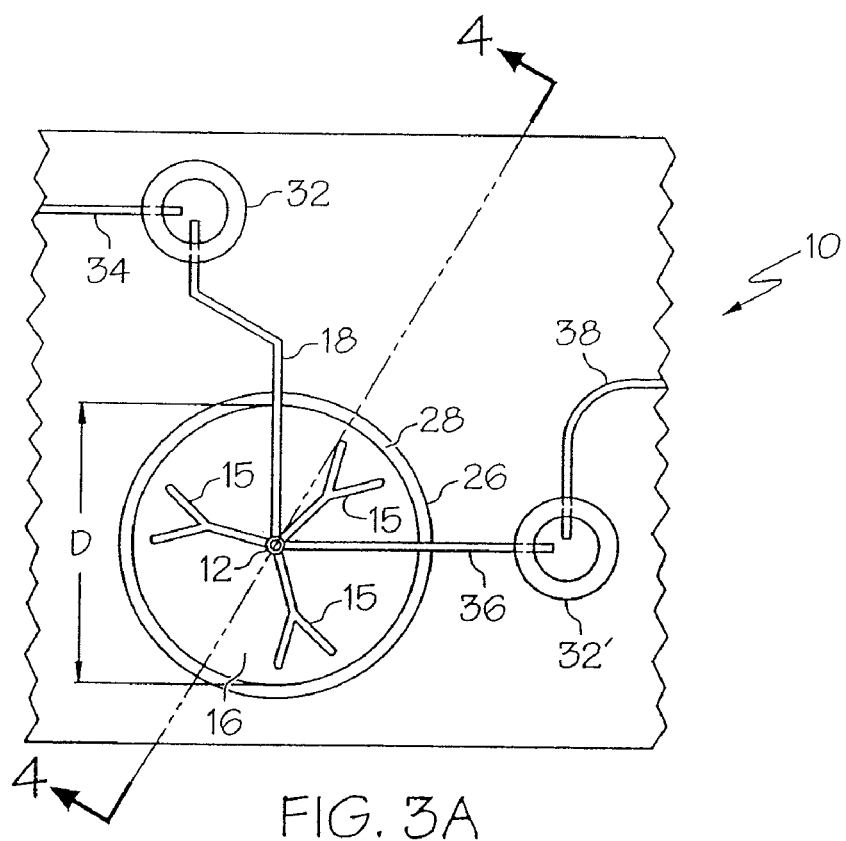
FIGS. 3A and 3B are top views of the micro-aliquotter of FIGS. 1 and 2 including two valves for controlling the flow of fluids into and out of the micro-aliquotter.
Figure 3B:
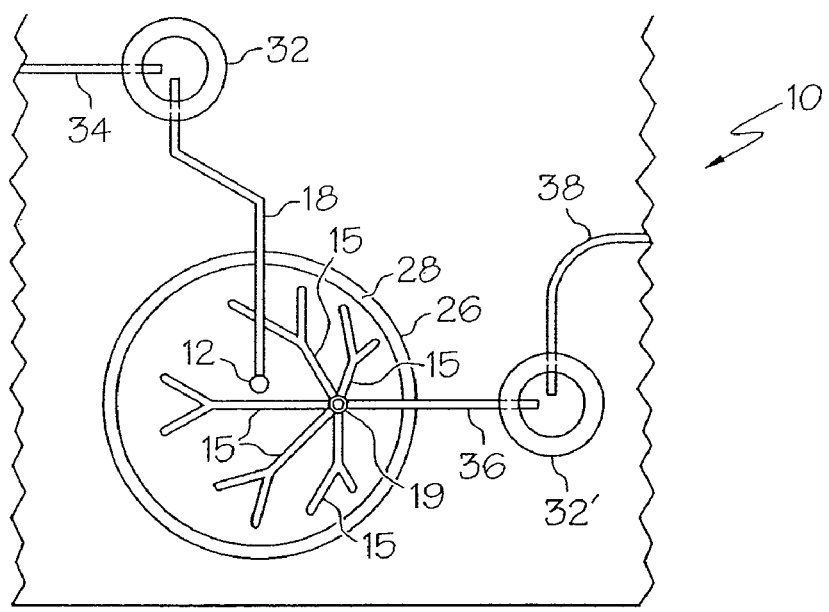

Now referring to FIGS. 3A and 3B, a top view of the micro-aliquotter is shown through multiple layers. An O-ring 28 is seen within an annular channel 26. To be able to contain and later discharge the aliquot volume from under the elastic film 16, the first channel 18 and an exit channel 36 may include valves 32 and 32' respectively, which in this embodiment are two-way diaphragm valves integral to the fluidic. The first channel 18 and the exit channel 36 may both be in fluid communication with the fluid port 12. The micro-aliquotter may also include connecting channels 34 and 38 that connect the valves 32 and 32', respectively, to other channels or features of the microfluidic device. The micro-aliquotter may also include very shallow surface features 15 that promote complete dispensing the aliquot volume from the device. In the embodiment shown in FIGS. 3A, the surface features 15 are recesses or scratches in the surface of the foundational layer that assist the aliquot volume in draining from under the film and toward the fluid port 12 during dispensing. The recessed surface features 15 may have a gradual slope or taper toward the fluid port. Alternately, as shown in FIG. 3B, the micro-aliquotter may include an outlet port 19 in fluid communication with an outlet channel 36 and surface features 15 that extend from near the periphery of the aliquot chamber to an outlet port 19 under the film that is separate from the fluid port 12.

Figure 4:
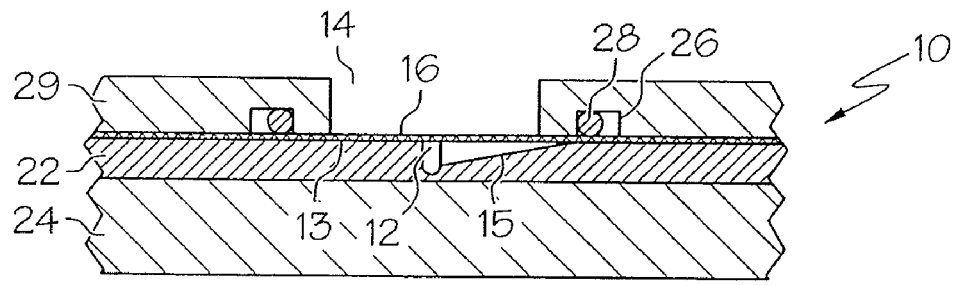
FIG. 4 is a cross-section view of the micro-aliquotter of FIG. 3A along line 4-4.

FIG. 4 shows the recessed surface features 15 of FIG. 3A in cross-section. The surface features 15 may be as simple as a few scratches scored on the surface of the foundational layer 22. As shown, the surface features 15 may slope toward and join the fluid port 12 or alternately an outlet port. While recessed surface features 15 may affect the accuracy of the aliquot volume 21 by retaining a small portion of the fluid, the amount will be very low and the aliquot volume that is actually discharged should still be reproducible. The size of the recessed surface features should be balanced against the flexibility characteristics of the elastic film. The recessed surface features should be small enough that the elastic film does not extend and conform into the recessed surface features, which will allow the fluid to drain toward the fluid port 12. The surface features are advantageous because without them the elastic film 16, since it lies on the foundational layer and covers the fluid port, may seal the fluid port before the aliquot volume is completely discharged.

Figure 5:
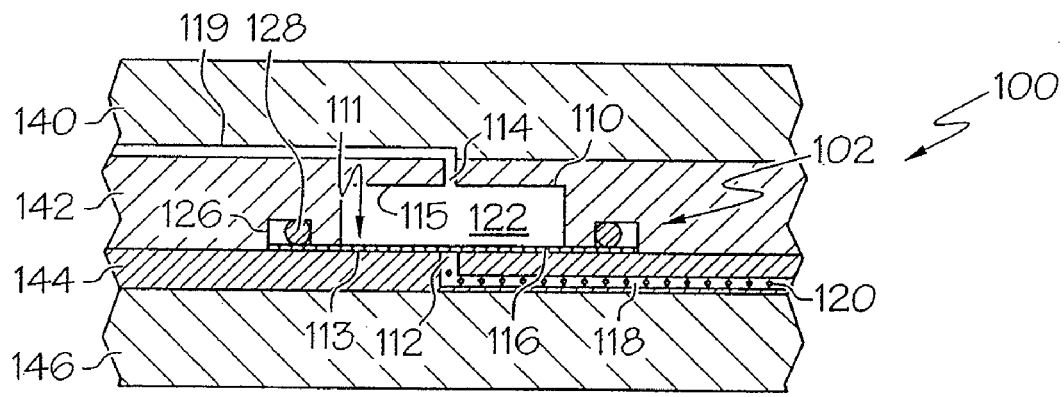
FIGS. 5 and 6 are partial sectional views of a microfluidic device showing a second embodiment of a micro-aliquotter.
Figure 6:
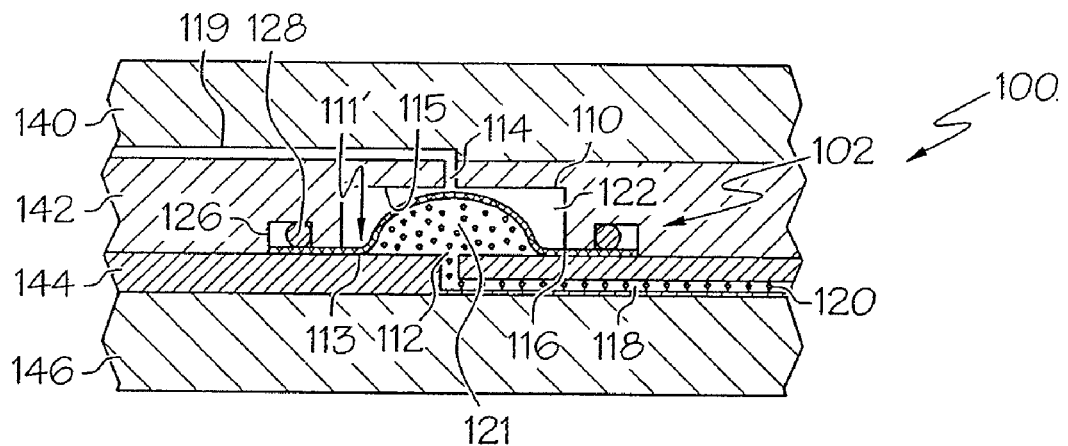

Referring to FIGS. 5 and 6, a portion of a microfluidic device, generally designated 100, is shown that includes a micro-aliquotter 102 for metering an aliquot volume of a fluid. The micro-aliquotter 102 includes a chamber 110 that has a first fluid port 112 in a first wall 113 of the chamber and a second fluid port 114 in a second wall 115. The first fluid port 112 may be in communication with a first channel 118 in the microfluidic device 100 for a first fluid to move from the first channel 118 through the first fluid port 112 into the chamber 110 and/or the reverse. Likewise, the second fluid port 114 may be in communication with a second channel 119 in the microfluidic device 100 for a second fluid to move from the second channel 119 through the second fluid port 114 into the chamber 110 and/or the reverse.

The microfluidic device 100 may include a plurality of layers where the micro-aliquotter 102 may be formed in part in several layers. As seen in FIG. 5 and 6 the chamber portion of the micro-aliquotter is formed in a chamber layer 142. The first fluid port 112 is formed in a foundational layer 144 where a portion of the upper surface of the layer forms the first wall 113 of chamber 110. The foundational layer 144 may include the first channel 118 or a portion thereof. The second channel 119 may be formed in the chamber layer 142 or in a separate, external, layer 140, or partially in both layers. The microfluidic device may also include a substrate layer 146 to support the layers. The substrate layer 146 may be a substantially rigid, dimensionally stable layer as described above. The external layer 140, the chamber layer 142, and the foundational layer 144 may be of the same or different materials and may be any of the materials described above.

The micro-aliquotter 102 includes an elastic film 116 positioned within chamber 110 on the first wall 113 where the film covers the fluid port 112 and defines a fluid space 122 between the elastic film 116 and the chamber's second wall 115. The elastic film 116 may be made of or include one of the materials described above. The elastic film 116 is securely sealed against the first wall 113 so a first fluid entering through the fluid port 112 must be captured between the elastic film 116 and the first wall 113 and cannot flow through the elastic film 116 to the second fluid port 114 and a second fluid from the second fluid port 114 entering the chamber cannot flow to the first fluid port 112.

The elastic film 116 may have its perimeter fixed to the first wall 113 and/or extending between layers of the microfluidic device 100 or alternately may be fixed to another wall(s) of the chamber. As shown in FIGS. 5 and 6, the elastic film 116 may extend between layers 140 and 144 and include an annular channel 126 and an o-ring 128 for securing the elastic film 116 within the microfluidic device, as explained above. The elastic film 116 is fixed such that the film is expandable, particularly the central portion of the film, in response to a first fluid 120 moving through the first fluid port 112 into the chamber 110. The elastic film 116 is expandable from a rest position 111 on the first wall 113, shown in FIG. 5, to a dispensing position 111' having an aliquot volume 121 captured between the elastic film 116 and the first wall 113, as shown in FIG. 6. As the aliquot volume 121 increases, the fluid space 122 on the opposite side of the elastic film 116 decreases.

The aliquot volume 121 is dispensable by applying pressure above and/or to the elastic film 116. The second channel 119 may be connected to a reservoir containing a second fluid, for example air, contained under pressure and having a regulator. The channel 119 may include a valve (not shown) to control the flow of the second fluid into the channel and ultimately the chamber's fluid space 122. The compressed air may be allowed to flow into the fluid space 122 to exert increased pressure on the elastic film 116 when it is in the dispensing position to expel the aliquot volume 121 from under the film. The valve may also allow the second fluid within the fluid space 122 to be displaced therefrom when the first fluid 120 enters through the first fluid port 112 under increased fluid pressure and expands the elastic film 116.

Figure 7A:
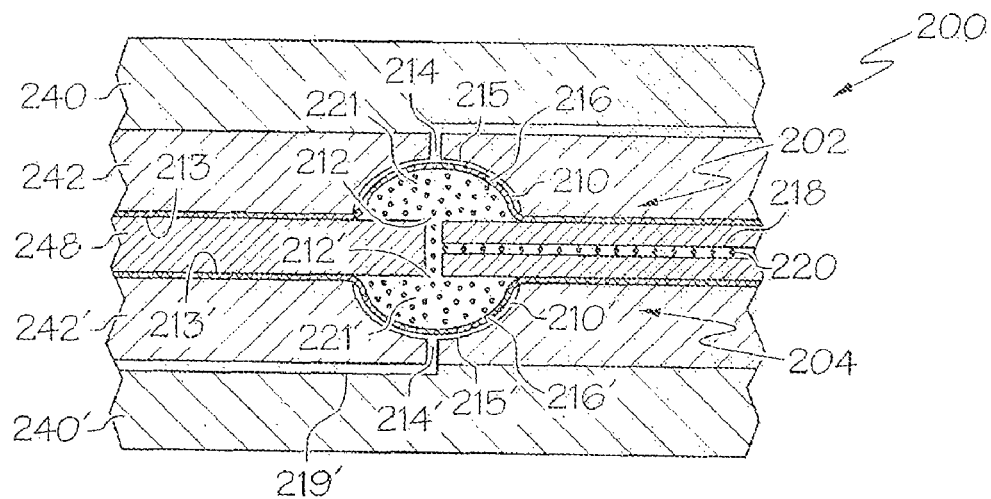
FIG. 7A is a partial sectional view of a microfluidic device showing an embodiment having two micro-aliquotters with their fluid ports in fluid communication with one another.

Now referring to FIG. 7A, a third embodiment of a microfluidic device, generally designated 200, is shown to include a first micro-aliquotter 202 and a second micro-aliquotter 204 that both may be similar to the micro-aliquotters described above in FIGS. 1-6. While FIG. 7A shows the two micro-aliquotters positioned on opposite sides of the foundational layer 248, the micro-aliquotters are not limited thereto. Instead, the plurality of micro-aliquotters may be adjacently positioned on the same surface of the foundational layer. The first and the second micro-aliquotters 202, 204 may include chambers 210, 210', respectively in a chamber layer 242 and 242'. In this embodiment, the first micro-aliquotter 202 includes a retention surface 215 that may define the maximum aliquot volume 221 and the second micro-aliquotter, likewise, includes a retention surface 215' that may define the maximum aliquot volume 221'. The retention surfaces 215, 215' each act as a stop that limits the movement of the elastic films 216, 216', respectively, and as such define the maximum aliquot volumes 221 and 221'. The retention surface may be the chamber's second wall or "inner surface." The inner surface in the embodiments described above were shown as generally flat surfaces in FIGS. 1-2 and 5-6. In this alternate embodiment, the inner surface is shown to be domed or semicircular in shape. A domed or semicircular inner surface is advantageous because the film is more likely to conform to such shapes when expanding in response to the first fluid, which enables the aliquot volume to more closely match the maximum volume defined by the chamber when in the dispensing position and thereby increasing the precision of the aliquot volume.

Figure 7B:
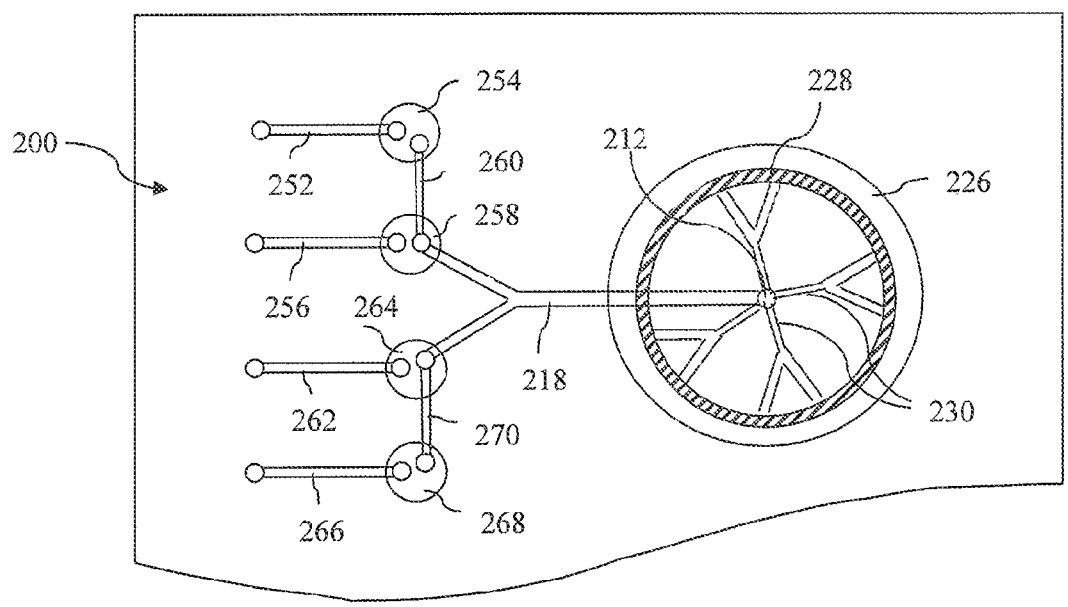
FIG. 7B is a top view of the micro-aliquotter of FIG. 7A including a plurality of fluid sources and fluid destinations.

In the embodiment shown in FIGS. 7A and 7B, each chamber 210, 210' includes a first fluid port 212 and 212', respectively, in fluid communication with one another. The fluid ports 212, 212' may also both be in fluid communication with a first channel 218 within the foundational layer 248 of the microfluidic device 200 that may contain a fluid 220. The foundational layer 248 may also contain the first fluid ports 212 and 212'. The micro-aliquotters 202 and 204 also include, respectively, second fluid ports 214, 214' in fluid communication with a second channel 219, 219', which may be in respective external layers 240 and 240'. The elastic films 216, 216' are positioned within the micro-aliquotters, as described above for the other embodiments, so the elastic films are expandable from a rest position on the foundational layer 248 to a dispensing position having an aliquot volume 221, 221' captured between the elastic films and the foundational layer 248. As seen in FIG. 7B, the micro-aliquotter may include an annular channel 226 and an O-ring 228 therein as described above. The micro-aliquotter 200 may also include surface features 230 similar to those described above.

The aliquot volumes 221, 221' may be the same or different volumes of the same or different fluids (or mixtures of fluids). For the micro-aliquotter to receive different fluids it may need to be connected to a plurality of fluid sources, for example fluid sources 252, 256 shown in FIG. 7B. The fluid sources 252, 256 may be connected to source valves 254, 258, respectively to control the flow of fluids into the micro-aliquotter. The source valves may be connected by channel 260.

The aliquot volumes 221, 221' may be discharged from the dispensing position by the application of pressure above and/or below to the elastic films 216, 216' respectively. As shown in FIGS. 7A and 7B, the fluid ports 212, 212' may both be in fluid communication with the first channel 218 and if the aliquot volumes 221, 221' are discharged through the first channel the aliquot volumes 221, 221' may be discharged to the same or different destination locations 262, 266. The discharge of the fluid from the micro-aliquotters may occur simultaneously or sequentially controlled through application of pressure above or below the elastic films and/or through the use of destination valves 264, 268. The destination valves 264, 268 may be connected by channel 270. In an alternate embodiment, the fluid ports 212, 212' may be in fluid communication with different channels, besides channel 218, within the microfluidic such that the aliquot volumes 221, 221' are discharged directly to different locations. This embodiment may include one or more additional fluid ports in communication with the aliquot volume for dispensing the fluid to the desired location(s). Dispensing from more than one aliquotter simultaneously through a shared channel has the effect of mixing the components while they are being transported. Sending the same solution to multiple destinations has utility when performing parallel analyses.

Figure 8:
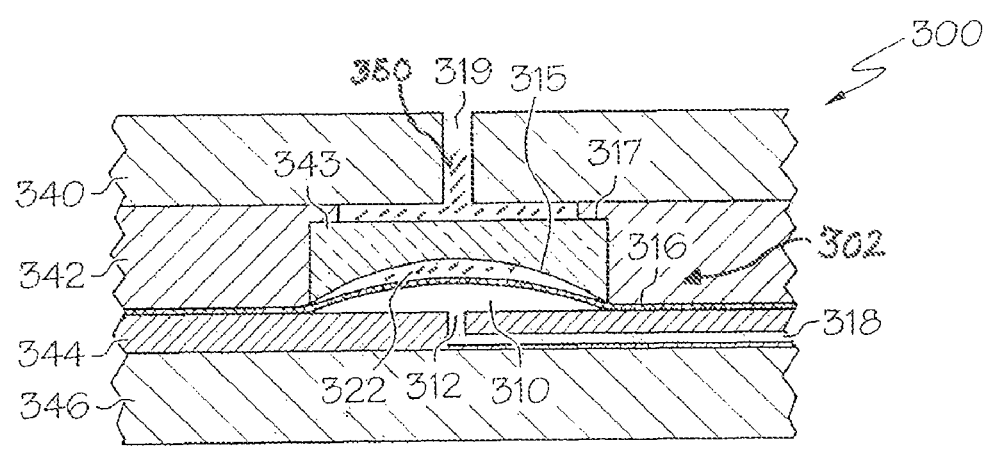
FIG. 8 is a partial sectional view of a microfluidic device showing a third embodiment of the micro-aliquotter.

When in the dispensing position, the elastic films 216, 216' may be pressed against the retention surfaces 215, 215', respectively, with enough fluid pressure from the first fluid 220 to expand slightly into the second fluid ports 214, 214'. This may cause the elastic film to rupture if the second fluid ports have sharp edges or over time from rubbing against the edges and/or walls of the second fluid ports. To reduce the occurrence of elastic film rupture, an alternate embodiment to having a retention surface with a second fluid port is shown in FIG. 8. FIG. 8 includes a portion of a microfluidic device 300 having a micro-aliquotter 302 that includes a microporous material or composition 343 that may include a microporous polyethylene, or microporous Teflon. The microporous material 343 conforms to the shape of a cavity 317 within the chamber layer 342 and allows a second fluid 350 to pass into and out of the fluid space 322 above the elastic film 316 through a plurality of micropores therein, which are small enough that the elastic film cannot conform into the pores. This is advantageous because the pores should not be able to rupture the elastic film. In one embodiment, the microporous material may form the entire chamber layer 342. The chamber may be milled, drilled, or ground into the microporous polyethylene using a generally spherically shaped bit. The microporous retention surface 315 should be in fluid communication with a channel 319 within the microfluidic device 300 to facilitate the transfer of fluids, for example air, into and out of the chamber 310 through the micropores. The channel 319 may be within the chamber layer 342, a fluidic layer 340, or partially formed in both layers. The micro-aliquotter 300, as shown, includes a foundational layer 344 having a fluid port 312 in fluid communication with a channel 318 within the microfluidic. The foundational layer 344 may be supported by a substrate 346. Otherwise, the micro-aliquotter 300 functions the same as the micro-aliquotters described above.

While the embodiments disclosed herein include channels connected to the fluid ports entering the micro-aliquotters, the microfluidic device may include additional microfluidic features known to one of skill in the art such as valves, additional channels and chambers, manifolds, reservoirs, or other features in various arrangements of fluid communication with the micro-aliquotter. The microfluidic device may include additional fluidic layers in order to include these additional microfluidic features, if needed. Any of the channels, chambers, ports, and other microfluidic features may be fabricated using known techniques including injection molding, micro-injection molding, embossing, casting, and surface etching, milling, and material known for use in such fabrication methods including the materials listed above for the substrate layer. The various layers of the microfluidic device may be connected or assembled to form the microfluidic by bonding, laminating, or adhering the layers together, or using other techniques known to one of skill in the art.

The micro-aliquotter, more specifically the aliquot volume defined by the film, has a width or diameter D shown in FIG. 3A that is about 3 to about 50 times that of the height H of the center portion of the film at a maximum aliquot volume shown in FIG. 2 At this aspect ratio, fluid can easily be made to enter the chamber in a turbulent manner, which is an aid to mixing, if multiple fluid species are present. The micro-aliquotter, for example in one embodiment, may have a diameter of about 0.335 inches with a height that ranges from about 0.01 inches to about 0.07 inches. The diameter of the micro-aliquotter may be equal to or greater than 0.1 inch. In an embodiment having a domed inner surface as the retention surface, like FIG. 7 or 8, the maximum aliquot volume defined by the location of the inner surface may be increased or decreased depending upon the diameter of the generally spherical bit used and the depth milled, drilled, or ground into the chamber layer. For example, for a chamber layer having a 0.335 in. diameter chamber blueprint for a micro-aliquotter, the maximum aliquot volume may be decreased as shown below, (i.e., the diameter will be maintained at 0.335 in.)

TABLE 1

| Max. Aliquot Volume (μL) | Diameter of the Spherical Bit (in.) | Depth Milled (in.) |
| --- | --- | --- |
| 32.3 | 0.500 | 0.0519 |
| 27.7 | 0.5625 | 0.0449 |
| 24.3 | 0.625 | 0.0397 |
| 19.7 | 0.750 | 0.0324 |
| 16.6 | 0.875 | 0.0274 |
| 13.3 | 1.000 | 0.0221 |

The micro-aliquotters disclosed herein aliquot accurate and precise volumes of fluids. To improve the accuracy, the micro-aliquotter should be run through a start up sequence to purge air or other entrapped gasses from the internal voids and from the fluid to be metered. Gases trapped in the micro-aliquotter can cause an error in metering the aliquot volume. Start up includes applying pressure above and to the elastic film to hold the film in the rest position while the channel leading to the fluid port under the film is filled. The fluid is pumped or pushed into and through the channels by increasing the fluid pressure of the fluid, as explained above. Next, the pressure holding the elastic film in the rest position is removed and the fluid in the channel is pushed through the fluid port by the increased fluid pressure and is captured between the elastic film and the foundational layer or the first wall to form the aliquot volume. If valves are being used, the valves in channels leading to and from the elastic film will need to be opened and closed appropriately. Then, pressure is reapplied above and/or to the elastic film to discharge, or drive, the aliquot volume from under the elastic film (i.e., moving the film from the dispensing position back to the rest position). The application of pressure should be a quick increase in pressure that will push or drive the solution from the micro-aliquotter to dispel entrapped air or other gases from the micro-aliquotter and/or the fluid. This may be repeated several times to remove the air or other gases. Once start up is complete, the micro-aliquotter is ready for use and it is should not be necessary to purge the system at a later time, but the process could be repeated if necessary.

The micro-aliquotters disclosed herein meters the aliquot volume with precision and/or accuracy even though the volumes are between about 5 μL to about 100 μL. The micro-aliquotters have the elastic film positioned on the foundational layer within the microfluidic device to allow the film to expand in response to a fluid as it is pumped up under the film. The film may expand to a plurality of aliquot volumes, which are thereafter dispensable. The accuracy of the micro-aliquotter is improved within the film positioned on the foundational layer or first wall of a chamber because the aliquot volume contained thereunder can be discharged completely such that the volume of fluid contained under the film is substantially zero.

With respect to the above embodiments, the micro-aliquotter uses the elastic film along with other rigid, dimensionally stable materials forming the chamber and the foundational layer such that the internal volume of the chamber is substantially constant while the aliquot volume is variable. When the micro-aliquotter includes a chamber the aliquot volume and the volume of the fluid space are inversely related because as the first fluid enters and is contained under the elastic film the film will extend into the chamber and decrease the fluid space. The aliquot volume is substantially zero when the elastic film is in the rest position. The aliquot volume is directly proportional to the amount the elastic film expands, thus the micro-aliquotter should be calibrated for each fluid to be aliquoted. The amount of expansion of the elastic film is related to the amount of fluid pressure applied to pump the fluid through the fluid port and under the film, the amount of time the fluid pressure is applied, the fluid used, and possibly the ambient conditions, such as temperature. The elastic film may be calibrated by pumping the fluid into the micro-aliquotter with gradually increasing fluid pressure for a set amount of time, for example 3 psi for 60 seconds, then 4 psi for 60 second, etc. and weighing the amount of fluid discharged each time and converting that to a volume based on the density of the fluid. Another calibration method utilizes applying a constant fluid pressure, for example 5 psi, and gradually increasing the time the fluid pressure is applied, for example 10 sec., 15 sec., 20 sec., etc. and again weighing the amount discharged and converting that to a volume determination.

The aliquot volume may be important for the analytical tests the microfluidic device is designed to run. In each embodiment, the accuracy of the aliquot volume may be affected by the volume of the channels, in particular fluids remaining in the dispensing or outlet channel leading from the micro-aliquotter. Accuracy is improved when the volume of the channels are small. The channels may be less than 100 microns in width or diameter, where the method of manufacturing the channel may limit how small the channels may be. Preferably the dispensing channel has a volume of a half a microliter or less. Depending upon the design used, the channel used to discharge the aliquot may be different from the channel used to load the aliquot. If this is true then there may be a small amount of dilution which occurs during dispensing of the aliquot. It is for this reason that the dispensing channel volume be kept as small as possible. Also, operationally, the user may wish to preload the dispense channel with the same solution as that being aliquoted, or some other fluid which would have no other effect than to dilute the aliquot in a minimal and repeatable way. There are several methods that may be used to meter the aliquot volume in the above embodiments of the micro-aliquotter. With respect to the micro-aliquotter shown in FIGS. 1-3 where the elastic film is open to the environment, the aliquot volume may be metered based upon the elasticity of the elastic film (a constant relationship between stress and strain) and the amount of pressure applied to the first fluid to move the first fluid under the elastic film. The film itself may be the source of pressure that drives the fluid from the micro-aliquotter as the elastic film wants to return to its unstretched state.

With respect to FIGS. 5 and 6, the fluid space within the chamber may be fillable with a second fluid that may enter and/or exit the fluid space through the second fluid port via the second channel. The second fluid should be impermeable to the flexible film and the other material(s) forming the chamber and second channel. The second fluid may be pumped into the fluid space in such a way that the volume, pressure, or amount of the second fluid is known. In one technique, a pre-selected volume or pressure of the second fluid is pumped into the fluid space to act as a stop via the pressure it applies to the elastic film to limit the expansion of the elastic film. This headspace pressure may be calibrated to correspond to a pre-selected aliquot volume that can be captured between the elastic film and the foundational layer in the dispensing position. The headspace pressure may be dependent upon the fluids used both in the fluid space and under the film. The fluid pressure pumping the fluid into the micro-aliquotter and the time such pressure is applied also affect the headspace pressure needed and are selected to reach the pre-selected aliquot volume. The micro-aliquotter used in this way is variable in that the volume or pressure of the second fluid may be controllable and measurable to supply different stop pressure and thereby allow different aliquot volumes to be aliquoted. One advantage of such a micro-aliquotter is the ability to vary the aliquot volume with reasonable precision from one volume to the next by simply changing the volume or pressure of the second fluid within the fluid space.

In an alternate method, the aliquot volume may be metered with precision by measuring the volume or pressure of the second fluid displaced from the fluid space by the aliquot volume. Here, the chamber starts with the fluid space containing an amount of the second fluid. Then some of the second fluid is displaced therefrom through the second fluid port in response to the collection of the aliquot volume between the elastic film and the foundational layer. The amount of second fluid displaced (i.e., by the volume, pressure, etc.) is measured and used to determine the aliquot volume relative thereto. In one embodiment the second fluid may be air.

The various embodiments of the micro-aliquotters described above may be used to meter a fluid volume. The method for metering the fluid volume includes providing one of the microfluidic devices described above, moving a first fluid from a channel through a fluid port to collect an aliquot volume of the fluid under the elastic film, and dispensing a metered aliquot volume. The aliquot volume may be discharged by the application of pressure above the flexible membrane to push or drive the aliquot volume out of the micro-aliquotter through the fluid port or an outlet port in fluid communication with the aliquot volume. The pressure may be applied by an increase in the amount of second fluid in the fluid space above the elastic film.

The fluid may be pumped into the micro-aliquotter as described above, i.e. under increased fluid pressure. The aliquot volume may be determined based on the pressure applied to move the fluid, the amount of time the pressure is applied, the elasticity of the elastic film, the position of a retention surface, by the amount of a second fluid in the fluid space above the elastic film, and/or by the amount of second fluid displaced from the fluid space, as explained above.

The micro-aliquotter may be calibrated by testing the particular elastic film with a particular fluid at various fluid pressures applied for a known amount of time for pumping the fluid into the micro-aliquotter.

EXAMPLE 1

A micro-aliquotter having a 0.001 inch thick polyurethane based elastic film exhibiting a durometer of 85 on the "A" scale of hardness, was calibrated with water. In the test configuration the fluidic, or foundational layer was made from polyimide film with channels having a cross section height of 75 microns and a width of 275 microns, approximately. The layer in which the retention chamber was formed was made from polycarbonate. The O-rings used to seal the elastic film to the foundational layer were made from silicone, and exhibited a hardness of 70 on the "A" scale. The water was driven into the micro-aliquotter using hydrostatic force from an external reservoir in which the headspace pressure was carefully controlled. Testing consisted of the discrete application of different pressures to the fluid headspace while observing the effect upon aliquoted volume's weight. For each pressure, the aliquot volume was discharged, collected, weighed, and converted to a volume using the density of water (assumed to be 1.0 g/ml). Here, the water was loaded at the selected fluid pressure for 60 seconds. Thereafter a pressure of about 7.0 psi was applied to the elastic film to discharge the aliquot volume by returning the elastic film to the rest position.

TABLE 2

| Fluid Pressure (psi) | load time (s) | Start Mass (mg) | End Mass (mg) | Volume Aliquoted (μL) |
|---|---|---|---|---|
| 1.0 | 60 | 20.6 | 33.8 | 13.2 |
| 1.5 | 60 | 33.8 | 59.5 | 25.7 |
| 2.0 | 60 | 59.5 | 89.3 | 29.8 |
| 2.5 | 60 | 89.3 | 121.4 | 32.1 |
| 3.0 | 60 | 121.4 | 155.3 | 33.9 |
| 3.5 | 60 | 155.3 | 189.8 | 34.5 |
| 4.0 | 60 | 189.8 | 224.5 | 34.7 |
| 4.5 | 60 | 224.5 | 258.9 | 34.4 |
| 5.0 | 60 | 258.9 | 293.6 | 34.7 |
| 5.5 | 60 | 293.6 | 327.9 | 34.3 |
| 6.5 | 60 | 32.7 | 67.1 | 34.4 |
| 7.0 | 60 | 67.1 | 101.8 | 34.7 |
| 7.5 | 60 | 101.8 | 136.8 | 35.0 |
| 8.0 | 60 | 136.8 | 171.8 | 35.0 |
| 8.5 | 60 | 171.8 | 206.9 | 35.1 |
| 9.0 | 60 | 206.9 | 241.6 | 34.7 |
| 9.5 | 60 | 241.6 | 276.5 | 34.9 |

Figure 9:
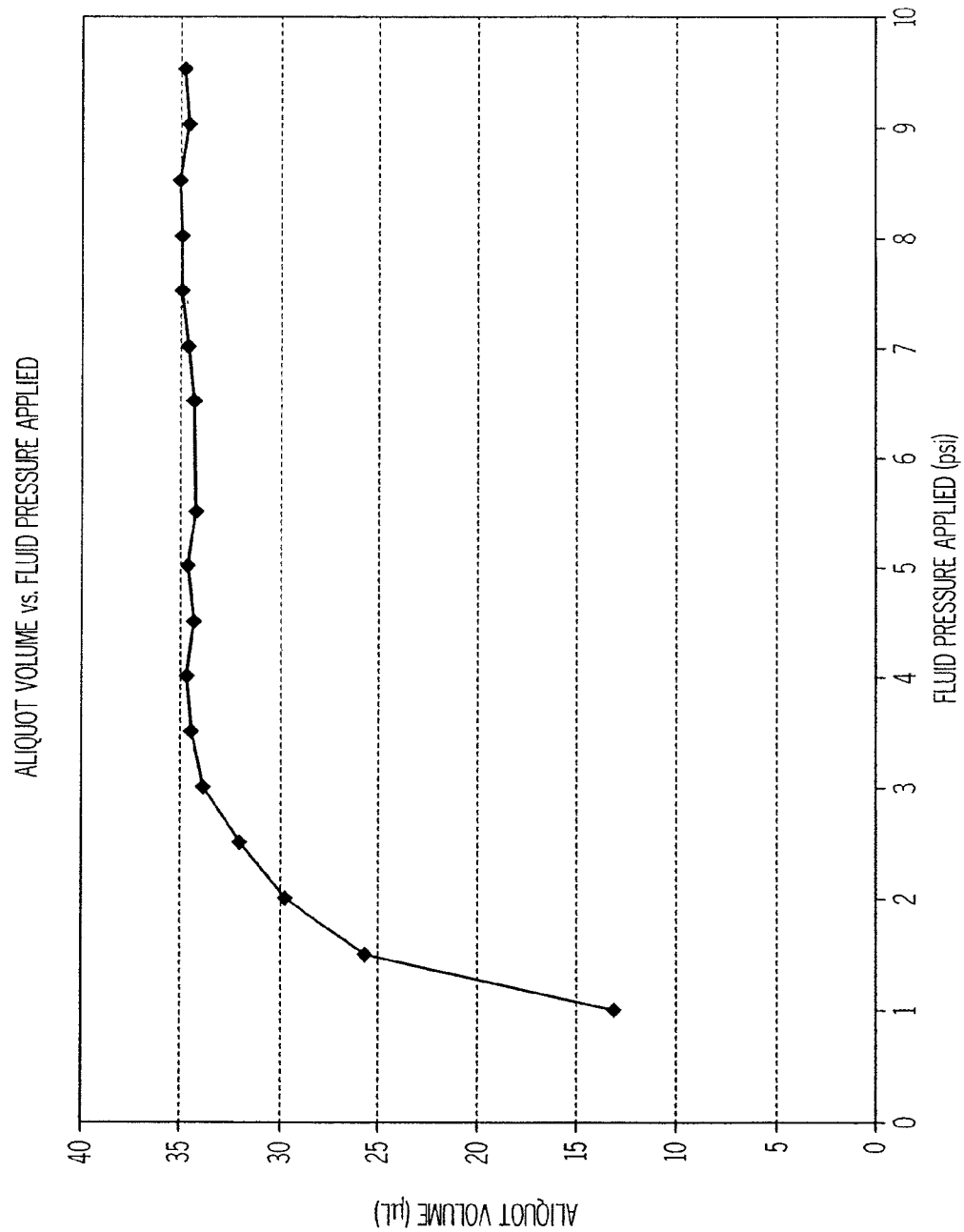
FIG. 9 is a graph of the relationship between the aliquot volume discharged and the fluid pressure applied to expand the elastic film to the dispensing position.

A graph of the data in Table 2 is included as FIG. 9. Note the plateau indicating that the aliquot volume had reached a maximum (i.e., the increase in pressure does not expand or stretch the flexible film any further). The plateau is represented by the last eleven data points in Table 2, which average to a maximum aliquot volume of 34.72 μL. The data indicates that a fluid pressure of about 4.0 psi and greater will reach the maximum aliquot volume of the elastic film in 60 seconds.

However, 60 seconds may be more time than is needed to reach the maximum aliquot volume.

EXAMPLE 2

In a configuration exactly like the one described in Example 1, water was pumped into the micro-aliquotter with a constant fluid pressure of 5 psi with increasing load times. The aliquot volume was discharged with a pressure of about 7.0 psi applied to the elastic film, collected, weighed, and converted to a volume assuming a density of 1.0 g/ml for the water.

TABLE 3

| Sample | Load Time (sec.) | Start Mass (mg) | End Mass (mg) | Aliquot Volume (µL) |
|---|---|---|---|---|
| 1 | 5 | 0 | 9.2 | 9.2 |
| 2 | 10 | 9.2 | 27.8 | 18.6 |
| 3 | 15 | 27.8 | 55.1 | 27.3 |
| 4 | 20 | 55.1 | 87.8 | 32.7 |
| 5 | 25 | 87.8 | 122.6 | 34.8 |
| 6 | 30 | 122.6 | 157.5 | 34.9 |
| 7 | 35 | 157.5 | 192.2 | 34.7 |
| 8 | 40 | 192.2 | 226.9 | 34.7 |

Figure 10:
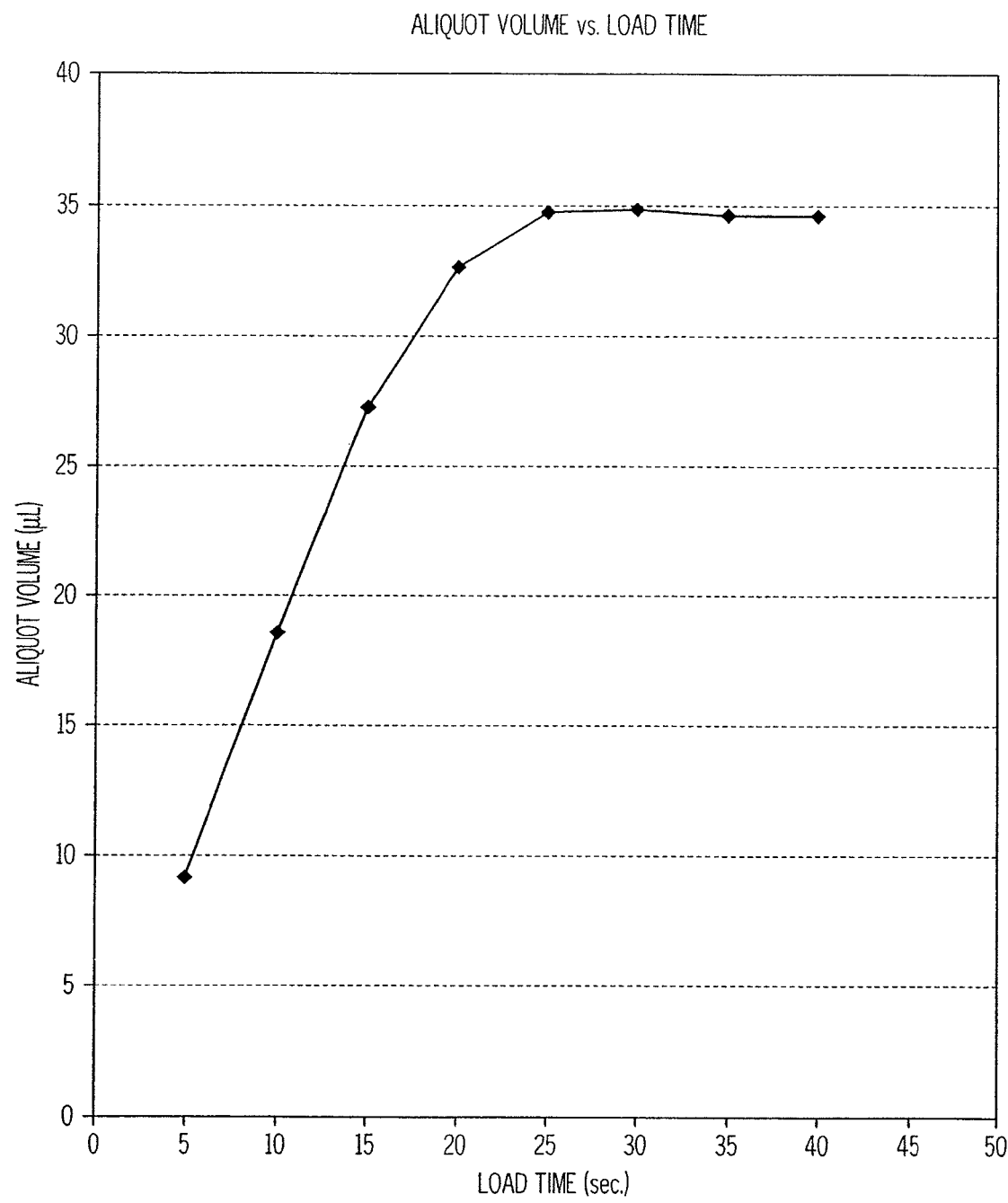
FIG. 10 is a graph of the relationship between the aliquot volume and the amount of time a constant fluid pressure was applied.

A graph of the data in Table 3 is included as FIG. 10. Note the plateau indicating that the aliquot volume has reached a maximum (i.e., the increase in load time does not move the flexible film any further). A fluid pressure of 5.0 psi will reach the maximum aliquot volume for this particular micro-aliquotter in 25 seconds.

Examples 1 and 2, above, focus on reaching the maximum aliquot volume for the elastic film, however, the micro-aliquotter is a variable micro-aliquotter that is capable of metering different volumes with the same micro-aliquotter. In Example 3 the micro-scale micro-aliquotter was tested at a fluid pressure for a load time that would not reach the maximum aliquot volume to test the precision of the micro-aliquotter.

EXAMPLE 3

A micro-aliquotter having a 0.0025 inch polyurethane based elastic film and other characteristics, otherwise, identical to those previously described in Example 1 was used for Example 3. Water was pumped into the micro-aliquotter with a constant fluid pressure of 3 psi for 60 sec., which is below the fluid pressure needed to reach the maximum aliquot volume (see Example 1). The aliquot volume was discharged with a pressure of about 7.0 psi applied to the elastic film, collected, weighed, and converted to a volume using the density of water.

TABLE 4

| Sample | Fluid Pressure (psi) | Load Time (sec.) | Start Mass (mg) | End Mass (mg) | Aliquot Volume (µL) |
|---|---|---|---|---|---|
| 1 | 3 | 60 | 0.0 | 23.8 | 23.8 |
| 2 | 3 | 60 | 23.8 | 47.8 | 24.0 |
| 3 | 3 | 60 | 47.8 | 71.1 | 23.3 |
| 4 | 3 | 60 | 71.1 | 86.1 | 15.0 |
| 5 | 3 | 60 | 86.1 | 109.4 | 23.3 |
| 6 | 3 | 60 | 109.4 | 132.8 | 23.4 |
| 7 | 3 | 60 | 132.8 | 156.6 | 23.8 |
| 8 | 3 | 60 | 156.6 | 179.8 | 23.2 |
| 9 | 3 | 60 | 179.8 | 203.1 | 23.3 |
| 10 | 3 | 60 | 203.1 | 226.6 | 23.5 |

The aliquot volume is reproducible, with the exception of outlier, sample 4. With sample 4 included the average aliquot volume is 22.66 µL with a standard error of 11.94%; however, without sample 4 the average aliquot volume is 23.51 µL with a standard error of only 1.21%.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

While specific innovative features may have been presented in reference to specific examples, they are just examples, and it should be understood that various combinations of these innovative features beyond those specifically shown are taught such that they may now be easily alternatively combined and are hereby anticipated and claimed.

What is claimed is:

1. A microfluidic device comprising at least one micro-aliquotter, the micro-aliquotter comprising:
   a rigid, dimensionally stable foundational layer having a fluid port therein, the fluid port being in fluid communication with a channel within the microfluidic device;
   an elastic film positioned on the foundational layer in a rest position with the elastic film lying on the foundational layer such that there is substantially little to substantially no space between the film and the foundational layer, wherein the elastic film covers the fluid port, the elastic film being sealed to the foundational layer at a distance removed from the fluid port so a fluid entering through the fluid port can be captured between the elastic film and the foundational layer; the elastic film being expandable from the rest position on the foundational layer to a dispensing position in which an aliquot volume of a fluid is contained between the film and the foundational layer; and
   a substrate layer supporting the foundational layer;
   wherein in the dispensing position the aliquot volume contained between the film and the foundational layer is about 5 µL up to about 100 µL.

2. The microfluidic device of claim 1 wherein the elastic film is expandable to a plurality of dispensing positions capturing different aliquot volumes; wherein one dispensing position is defined by the maximum aliquot volume that is containable between the film and the foundational layer.

3. The microfluidic device of claim 1 wherein the aliquot volume is meterable based on the elastic film's elasticity, the amount of pressure applied to move the first fluid through the fluid port, and the amount of time the pressure is applied.

4. The microfluidic device of claim 1 further comprising a layer that is positioned on the foundational layer over the elastic film, the layer having one or more surfaces therein that form a chamber, the chamber being fillable with a second fluid.

5. The microfluidic device of claim 4 wherein one surface of the one or more surfaces forming the chamber is an internal retention surface that defines the maximum aliquot volume.

6. The microfluidic device of claim 4 wherein by controlling the amount of the second fluid entering or being displaced from the chamber, the aliquot volume is controllable.

7. The microfluidic device of claim 6 wherein the amount of the second fluid in the chamber restricts the aliquot volume.

8. The microfluidic device of claim 1 wherein the channel includes a valve for controlling the flow of the fluid through the fluid port.

9. The microfluidic device of claim 8 further comprising a second fluid port in the upper surface of the foundational layer positioned under the elastic film, the second fluid port in fluid communication with a second channel that includes a second valve to control the dispensing of the aliquot volume.

10. The microfluidic device of claim 1 wherein the foundational layer contained under the elastic film includes recessed surface features to assist the fluid in draining to the fluid port and from under the elastic film.

11. The microfluidic device of claim 1 further comprising a second micro-aliquotter in fluid communication with the first micro-aliquotter; the second micro-aliquotter comprising:
 a second elastic film positioned on the foundational layer on a surface thereof that is opposite the surface having the fluid port for the first micro-aliquotter, the foundational layer further comprising a second fluid port therein that is in fluid communication with the fluid port of the first micro-aliquotter and in fluid communication with the channel within the microfluidic device, where the second elastic film covers the second fluid port, the second elastic film being sealed to the foundational layer at a distance removed from the second fluid port so the fluid entering through the second fluid port can be captured between the second elastic film and the foundational layer; the second elastic film being expandable from a rest position on the foundational layer to a dispensing position in which an aliquot volume of the fluid is contained between the film and the foundational layer.

12. A microfluidic device comprising at least one micro-aliquotter, the micro-aliquotter including:
 a chamber layer having a chamber, the chamber layer having a first fluid port in a first wall that defines at least part of the chamber and a second fluid port in a second wall that defines at least part of the chamber, the first fluid port being in communication with a first channel in the microfluidic device and the second fluid port being in communication with a second channel in the microfluidic device, the first wall being part of a rigid, dimensionally stable foundational layer that has the chamber layer thereon; and
 an elastic film positioned on the first wall in a rest position with the elastic film lying on the first wall such that there is substantially little to substantially no space between the film and the foundational layer, wherein the elastic film covers the first fluid port and defines a space between the second wall and the elastic film; the elastic film being sealed within the microfluidic device so a first fluid entering through the first fluid port can be captured between the film and the first wall and cannot flow to the second fluid port and a second fluid from the second fluid port cannot flow to the first fluid port;
 wherein the elastic film captures an aliquot volume between the elastic film and the first wall in response to the first fluid moving into the chamber through the first fluid port; the elastic film being expandable from the rest position on the foundational layer to a dispensing position in which an aliquot volume of the first fluid is contained between the film and the foundational layer;
 wherein the aliquot volume contained between the film and the first wall is a volume of about 5 µL up to a volume of about 100 µL.

13. The microfluidic device of claim 12 wherein the aliquot volume is variable.

14. The microfluidic device of claim 12 wherein the aliquot volume is meterable based on the elastic film's elasticity, the amount of pressure applied to move the fluid through the first fluid port, and the time the pressure is applied.

15. The microfluidic device of claim 12 wherein the chamber includes an internal retention surface or an internal retention pressure that defines the maximum aliquot volume.

16. The microfluidic device of claim 15 wherein the retention surface includes a microporous polymer.

17. The microfluidic device of claim 15 wherein the internal retention pressure is a headspace pressure of a preselected amount of a second fluid filling the fluid space.

18. The microfluidic device of claim 12 wherein by controlling the amount of the second fluid entering or being displaced from the chamber, the aliquot volume is controllable.

19. The microfluidic device of claim 12 further comprising a second micro-aliquotter in fluid communication with the first micro-aliquotter.

20. A method for metering a fluid volume in a microfluidic device, the method comprising:
 a) providing a micro-aliquotter, the micro-aliquotter comprising:
 a rigid, dimensionally stable foundational layer having a fluid port therein, the fluid port being in fluid communication with a channel within the microfluidic device; and
 an elastic film positioned on the foundational layer in a rest position with the elastic film lying on the foundational layer such that there is substantially little to substantially no space between the film and the foundational layer, wherein the elastic film covers the fluid port, the elastic film being sealed to the foundational layer at a distance removed from the fluid port so a fluid entering through the fluid port can be captured between the elastic film and the foundational layer; the elastic film being expandable from the rest position on the foundational layer to a dispensing position in which an aliquot volume of the fluid is contained between the film and the foundational layer;
 a substrate layer supporting the foundational layer;
 wherein in the dispensing position the aliquot volume contained between the film and the foundational layer is about 5µL up to about 100 µL;
 b) providing a fluid in the channel;
 c) loading an aliquot volume of the fluid between the elastic film and the foundational layer; and
 d) dispensing the aliquot volume.

21. The method of claim 20 wherein loading of the aliquot volume includes an increase of fluid pressure on the fluid to move the fluid through the fluid port.

22. The method of claim 21 wherein the aliquot volume is meterable based on the fluid pressure applied to the fluid to load the aliquot volume, the elasticity of the elastic film, and the time the fluid pressure is applied.

23. The method of claim 20 wherein the micro-aliquotter further comprises a chamber layer having one or more walls defining a chamber therein that includes a second fluid port entering the chamber, the chamber layer positioned on the foundational layer with the chamber over the elastic film to define a fluid space between the elastic film and the one or more walls defining the chamber, the fluid space being in fluid communication with the second fluid port.

24. The method of claim 23 wherein an internal retention surface or an internal pressure that the elastic film stops against is present within the chamber and defines the maximum aliquot volume.

25. The method of claim 24 wherein the internal retention pressure is a headspace pressure applied by a preselected amount of a second fluid filling the fluid space.

26. The microfluidic device of claim 23 wherein the fluid space is fillable with a second fluid that is displaceable from the chamber through the second fluid port in response to the first fluid forming an aliquot volume, wherein the amount of second fluid displaced is measurable for determining the aliquot volume of the first fluid.

* * * * *